(12) United States Patent
Ann (10) Patent No.: US 12,246,138 B2
(45) Date of Patent: Mar. 11, 2025

(54) LIQUID MEDICATION-INJECTING URINARY CATHETER

(71) Applicant: EZUROTECH CO., LTD., Seoul (KR)

(72) Inventor: Hyang Nam Ann, Seoul (KR)

(73) Assignee: EZUROTECH CO., LTD., Seoul (KR)

( * ) Notice: Subject to any disclaimer, the term of this patent is extended or adjusted under 35 U.S.C. 154(b) by 0 days.

(21) Appl. No.: 18/588,390

(22) Filed: Feb. 27, 2024

(65) Prior Publication Data
US 2024/0198040 A1 Jun. 20, 2024

Related U.S. Application Data

(63) Continuation of application No. PCT/KR2022/006752, filed on May 11, 2022.

(30) Foreign Application Priority Data

Feb. 16, 2022 (KR) ........................ 10-2022-0019841

(51) Int. Cl.
*A61M 25/00* (2006.01)
*A61M 27/00* (2006.01)

(52) U.S. Cl.
CPC .... *A61M 25/0017* (2013.01); *A61M 25/0026* (2013.01); *A61M 25/007* (2013.01); *A61M 27/008* (2013.01); *A61M 2025/0037* (2013.01); *A61M 2210/1089* (2013.01)

(58) Field of Classification Search
CPC .......... A61M 25/0017; A61M 25/0026; A61M 25/007; A61M 27/008; A61M 2025/0037; A61M 2210/1089
See application file for complete search history.

(56) References Cited

U.S. PATENT DOCUMENTS

| | | | | |
|---|---|---|---|---|
| 3,516,410 A | * | 6/1970 | Hakim | A61M 25/04 604/268 |
| 3,583,404 A | * | 6/1971 | McWhorter | A61M 27/008 604/266 |
| 4,501,580 A | * | 2/1985 | Glassman | A61M 25/0017 604/102.01 |
| 4,579,554 A | * | 4/1986 | Glassman | A61M 25/0017 604/103.08 |
| 4,809,710 A | * | 3/1989 | Williamson | A61M 25/007 600/593 |

(Continued)

FOREIGN PATENT DOCUMENTS

| | | | | |
|---|---|---|---|---|
| CN | 111001048 A | * | 4/2020 | .......... A61M 1/0062 |
| CN | 113440658 A | * | 9/2021 | |

(Continued)

OTHER PUBLICATIONS

International Search Report (PCT/ISA/210) issued in PCT Application No. PCT/KR2022/006752 dated Nov. 11, 2022 with English Translation.

(Continued)

*Primary Examiner* — Adam Marcetich
(74) *Attorney, Agent, or Firm* — Morgan, Lewis & Bockius LLP (57) ABSTRACT

The present disclosure relates to a medical liquid-injecting urinary catheter including a catheter body, an inflation tube, a urination port, an air injection port, and a medical liquid-injection port.

19 Claims, 12 Drawing Sheets

(56) References Cited

U.S. PATENT DOCUMENTS

| | | | | |
|---|---|---|---|---|
| 5,271,735 A * | 12/1993 | Greenfeld | A61M 25/0068 604/35 |
| 5,562,622 A * | 10/1996 | Tihon | A61M 27/008 604/105 |
| 5,688,239 A * | 11/1997 | Walker | A61F 2/0022 604/27 |
| 5,738,654 A * | 4/1998 | Tihon | A61F 2/04 604/105 |
| 6,080,142 A * | 6/2000 | Sachse | A61F 2/0027 604/326 |
| 7,223,263 B1 * | 5/2007 | Seno | A61M 1/285 604/537 |
| 2002/0082547 A1 * | 6/2002 | Deniega | A61M 25/0074 604/93.01 |
| 2002/0095198 A1 * | 7/2002 | Whitebook | A61M 25/0017 607/101 |
| 2003/0216710 A1 * | 11/2003 | Hurt | A61M 25/007 604/537 |
| 2010/0076425 A1 * | 3/2010 | Carroux | A61B 18/1485 606/41 |
| 2013/0245555 A1 * | 9/2013 | Dirac | A61M 5/158 604/174 |
| 2014/0336624 A1 * | 11/2014 | Adams, Jr. | A61M 25/1002 604/544 |
| 2016/0367747 A1 * | 12/2016 | Loske | A61M 25/007 |
| 2017/0080178 A1 * | 3/2017 | O'Connell | A61M 25/005 |

FOREIGN PATENT DOCUMENTS

| | | | |
|---|---|---|---|
| CN | 113908404 A * | 1/2022 | |
| FR | 2940914 A1 * | 7/2010 | A61M 25/0021 |
| KR | 10-1999-0064051 A | 7/1999 | |
| KR | 10-2002-0023956 A | 3/2002 | |
| KR | 10-2019-0112010 A | 10/2019 | |
| KR | 10-2021-0027945 A | 3/2021 | |
| KR | 10-2021-0064673 A | 6/2021 | |
| WO | WO-2021185931 A2 * | 9/2021 | |

OTHER PUBLICATIONS

Korean language Written Opinion (PCT/ISA/237) issued in PCT Application No. PCT/KR2022/006752 dated Nov. 11, 2022.

\* cited by examiner

LIQUID MEDICATION-INJECTING URINARY CATHETER

TECHNICAL FIELD

The present disclosure relates to a medical liquid-injecting urinary catheter, and more particularly, to a medical liquid-injecting urinary catheter that is configured to supply medical liquid to the urethra and bladder and is easily inserted into the urethra to prevent from causing pain.

BACKGROUND ART

Figure 1:
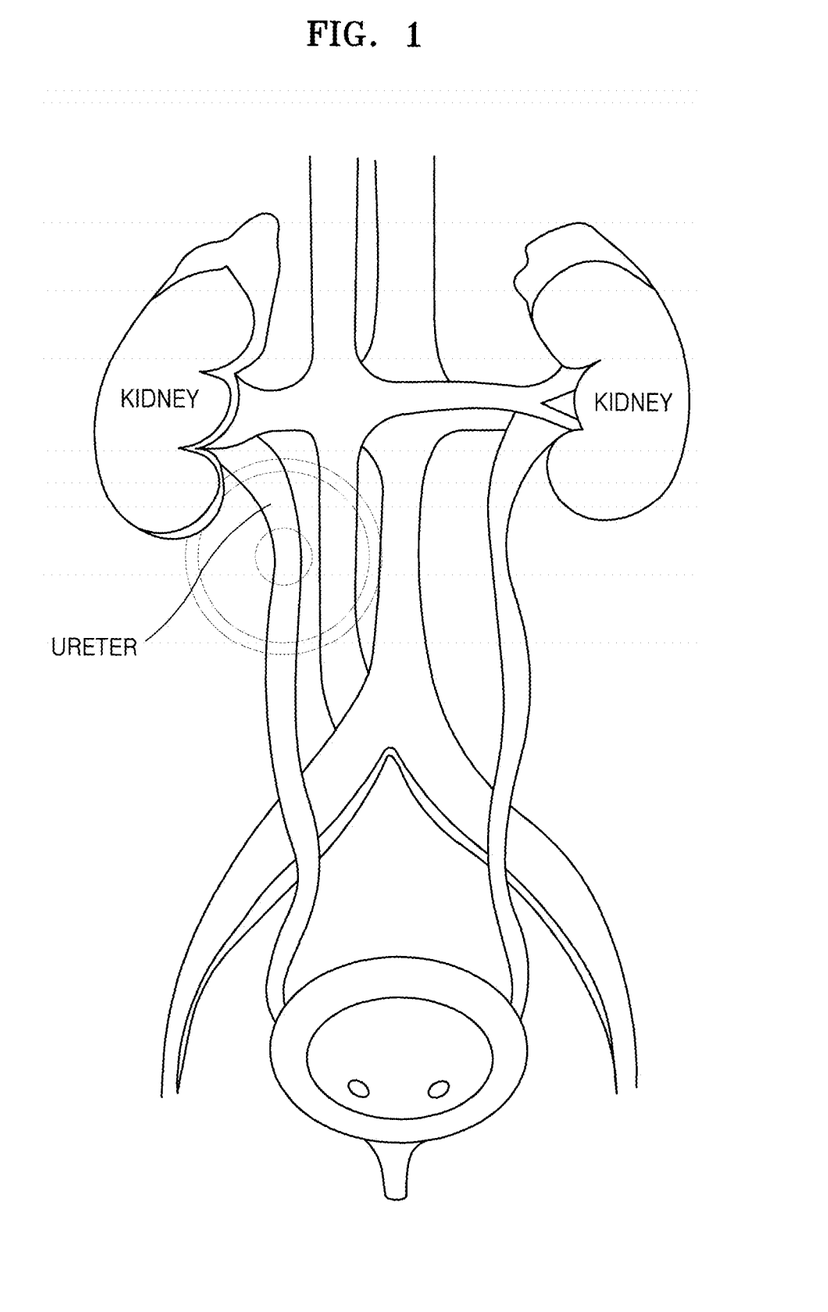
FIG. 1 is a view illustrating a urination structure of a body.

As illustrated in FIG. 1, urine excreted from the kidneys is transported to the bladder through the ureters and excreted out of the body through the urethra.

On the other hand, when patients have difficulties in voluntarily excreting urine, a flexible tube such as a catheter is inserted into the bladder through the urethra to excrete urine.

At this time, when there is a need for the prevention of bacterial contamination due to the catheter, topical anesthesia, antibiotics or topical anesthetics are injected from the outside through the catheter and supplied to the bladder or urethra.

Figure 2A:
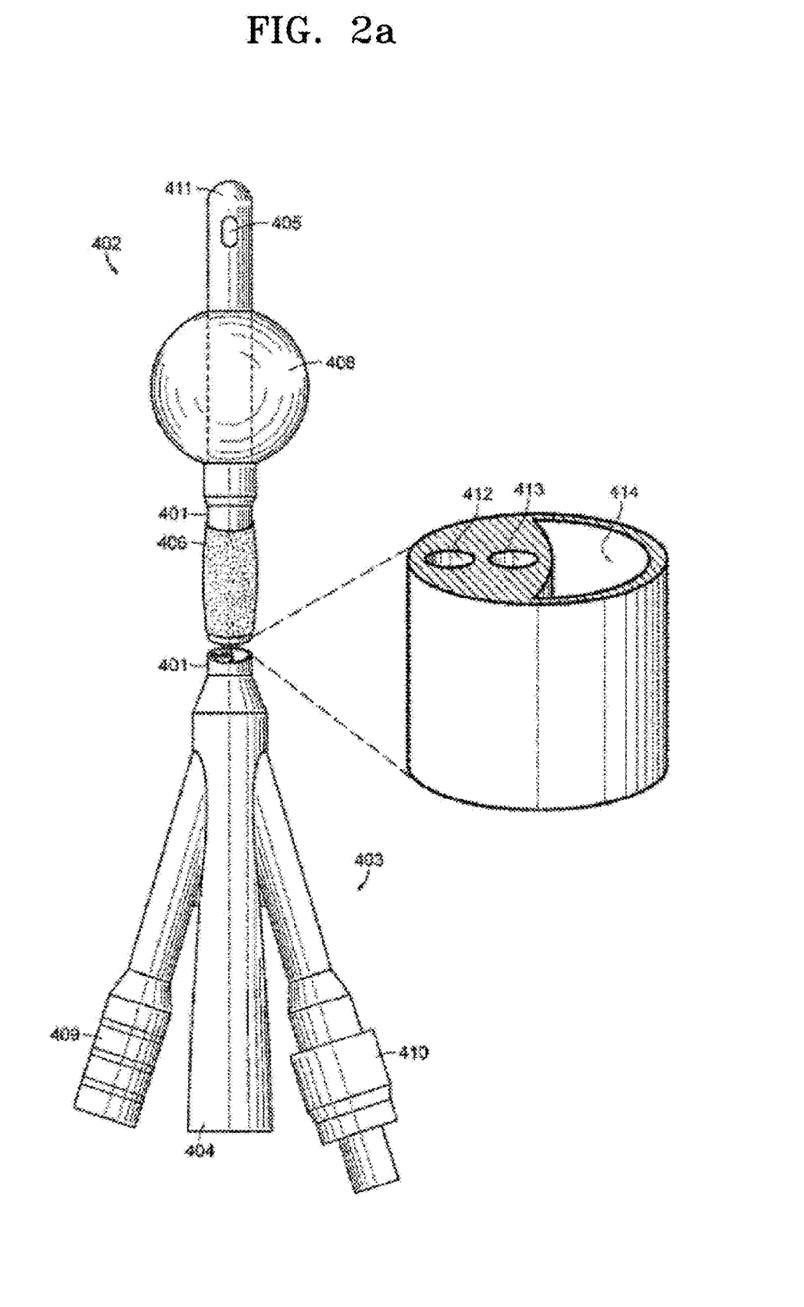
FIGS. 2A and 2B are views illustrating a structure of a catheter for urination according to the prior art.
Figure 2B:
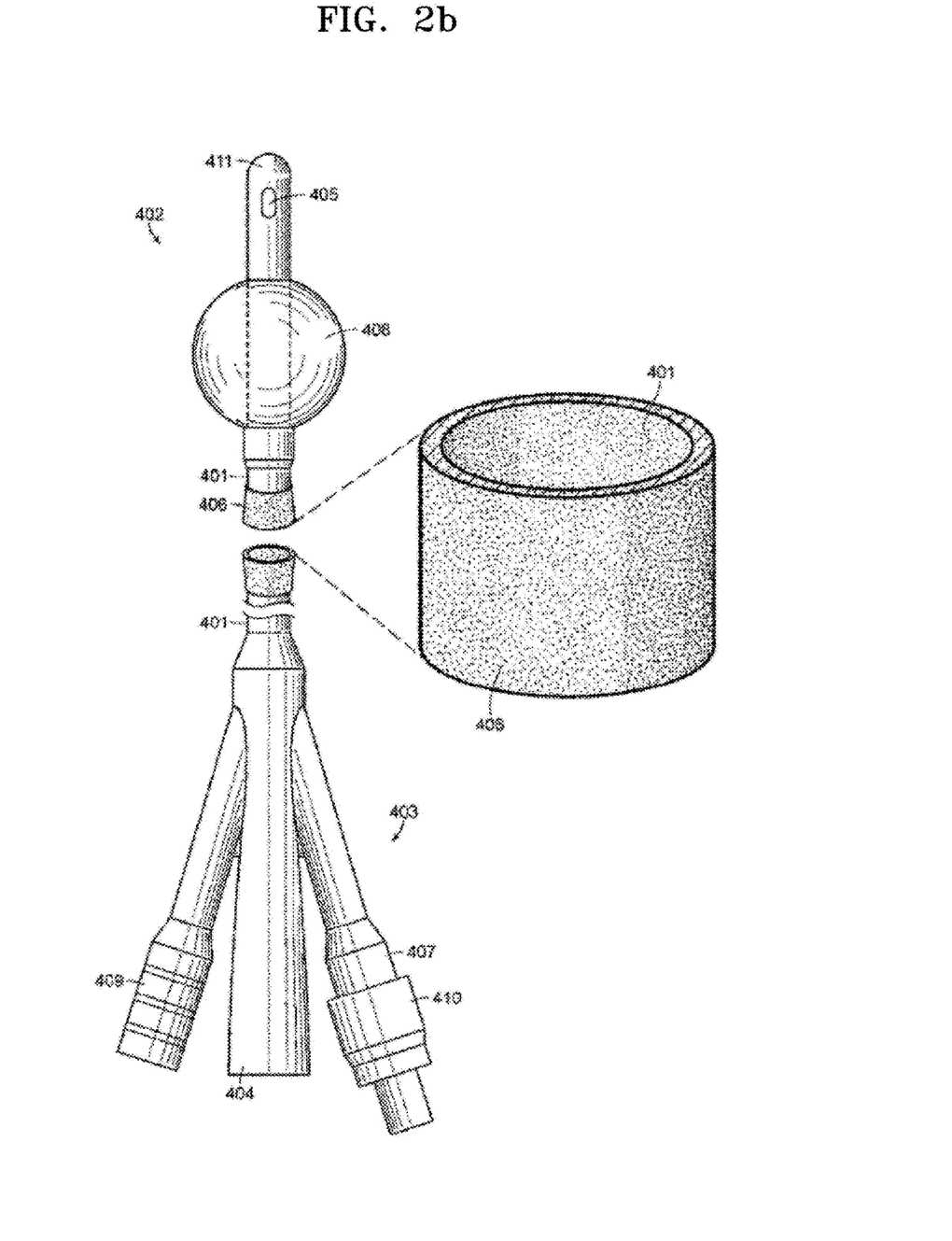

The representative configuration of these catheters is disclosed in [Prior Art Document 1], and is schematically described with reference to FIGS. 2A and 2B as follows.

As illustrated, the catheter of [Prior Art Document 1] includes an elongated tubular catheter body 401 having a distal end 402 and a proximal end 403, and the excretion lumen 404 extends from the distal end 402 to the proximal end 403 through the tube 414 in the catheter body 401.

When the excretion lumen 404 is used to excrete urine from the bladder of the patient by communicating with an opening or an eyelet 405 in the catheter body 401 at the distal end 402 of the catheter body 401, urine may flow into the excretion lumen 404 through the eyelet 405.

In addition, a sleeve portion 406 composed of a semipermeable membrane is formed on the catheter body 401.

An instillation lumen 410 extends from the catheter body 401 at the proximal end 403.

The instillation lumen 410 is connected to the sleeve portion 406 by using a tube 413 extending along the longitudinal direction of the catheter body 401.

Medical liquid injected into the sleeve portion 406 through the tube 413 continuously cleans the space around the urethra to prevent the formation of a biological membrane and subsequent bacterial infection.

That is, the medical liquid is supplied to the inner circumferential surface of the urethra through the sleeve portion 406 composed of a semi-permeable membrane, to thereby exert medicinal effects.

The fluid may include preservatives, antibiotics, or antimicrobials, and/or a combination thereof to prevent bacterial infection of urethra in contact with the catheter body.

An inflation fluid passes through an inflation lumen 409 and a tube 412 in the catheter body 401 to inflate a tube section 408.

However, according to the [Prior Art Document 1], since the separately provided sleeve portion 406 is coupled to the catheter body 401, there has no choice but to be discontinuous in terms of material and shape, and accordingly, the catheter has difficulties in being inserted into the urethra and pain caused by friction occurs in the insertion process, which increases inconveniences of the patient.

PRIOR ART DOCUMENT

[Prior Art Document 1] Korean patent publication No. 10-2019-0112010 (2019 Oct. 2)

DETAILED DESCRIPTION OF INVENTION

Technical Problem

The present disclosure is contrived for solving the problems of the prior art described above, and an object of the present disclosure is to provide a medical liquid-injecting urinary catheter which is easily inserted into the urethra and significantly reduces the occurrence of pain.

In addition, another object of the present disclosure is to provide a medical liquid-injecting urinary catheter capable of maximizing the medicinal effect of the supplied medical liquid.

Technical Solution to Problem

In order to achieve the above-described object, the medical liquid-injecting urinary catheter according to the present disclosure is characterized in that the medical liquid-injecting urinary catheter includes
  a catheter body that is flexible and has a hollow pipe shape;
  an inflation tube positioned around one end of the catheter body and spaced apart from the one end;
  a urination port connected to the other end of the catheter body and excreting urine out of the body;
  an air injection port connected to the other end of the catheter body and injecting air into the expansion tube; and
  a medical liquid-injection port connected to the other end of the catheter body and injecting a medical liquid,
  wherein,
  in a cross-sectional view of the hollow, a urination hole communicating with the urination port, an air injection hole communicating with the air injection port, and a medical liquid-injection hole communicating with the medical liquid-injection port are arranged to be separated from each other, and
  a plurality of medical liquid discharge outlets are formed on a circumferential surface of the catheter body in such a configuration that the plurality of medical liquid discharge outlets communicate with the medical liquid-injection hole and are spaced apart from each other in a direction in which the catheter body extends.

It is characterized in that a plurality of ring-shaped medical liquid distribution grooves extending in a circumferential direction of the catheter body are formed to be spaced apart from each other in the direction in which the catheter body extends, and the medical liquid discharge outlet is formed in each of the ring-shaped medical liquid distribution grooves.

Alternatively, it is characterized in that a spiral medical liquid distribution groove spirally extending in a circumferential direction of the catheter body is formed in the direction in which the catheter body extends, and the medical liquid discharge outlets are formed in the spiral medical liquid distribution grooves, respectively.

It is characterized in that the medical liquid discharge outlets are formed to be spaced apart from each other on a virtual line that is on the circumferential surface parallel to a cross-sectional center line of the catheter body, and in a cross-sectional view of the catheter body, the medical liquid discharge outlets are formed to be inclined with respect to a radial direction of the catheter body.

It is characterized in that the medical liquid discharge outlets are formed to be alternately inclined in opposite directions about the radial direction of the catheter body along a longitudinal direction of the catheter body.

It is characterized in that the medical liquid discharge outlets are arranged on a virtual spiral along the circumferential surface of the catheter body.

It is characterized in that, in a cross-sectional view of the catheter body, the catheter body includes
- a first tube shaped as a circle and having inner and outer circumferential surfaces,
- a second tube protruding from the inner circumferential surface of the first tube in an arc shape to form the air injection hole,
- and a third tube protruding from the inner circumferential surface of the first tube in an arc shape to form the medical liquid-injection hole and spaced apart from the second tube in the circumferential direction, wherein
an inside of the first tube, which is formed at outsides of the second tube and the third tube, forms the urination hole.

Advantageous Effects of Invention

According to the present disclosure having the configurations described above, since there is provided a medical liquid-injecting urinary catheter including a catheter body that is flexible and has a hollow pipe shape, an inflation tube positioned around one end of the catheter body and spaced apart from the one end, a urination port connected to the other end of the catheter body and excreting urine out of the body, an air injection port connected to the other end of the catheter body and injecting air into the expansion tube, and a medical liquid-injection port connected to the other end of the catheter body and injecting a medical liquid wherein in a cross-sectional view of the hollow, a urination hole communicating with the urination port, an air injection hole communicating with the air injection port, and a medical liquid-injection hole communicating with the medical liquid-injection port are arranged to be separated from each other, and a plurality of medical liquid discharge outlets are formed on a circumferential surface of the catheter body in such a configuration that the plurality of medical liquid discharge outlets communicate with the medical liquid-injection hole and are spaced apart from each other in a direction in which the catheter body extends, there are advantages in that a predetermined function such as the topical anesthesia and the bladder cleaning is performed in a longitudinal direction of the urethra by applying the medical liquid passing through the medical liquid-injection port and the medical liquid-injection hole to the bladder or the urethra through the medical liquid discharge outlet, the medical liquid is easily inserted into the urethra, and the occurrence of pain is significantly reduced.

In addition, according to the present disclosure, since, in a cross-sectional view of the catheter body, the catheter body includes a first tube shaped as a circle and having inner and outer circumferential surfaces, a second tube protruding from the inner circumferential surface of the first tube in an arc shape to form the air injection hole, and a third tube protruding from the inner circumferential surface of the first tube in an arc shape to form the medical liquid-injection hole and spaced apart from the second tube in the circumferential direction, wherein an inside of the first tube, which is formed at the outsides of the second tube and the third tube, forms the urination hole, the obstruction of the hollow and topical pain caused by discontinuous bending of the catheter body may be prevented when the catheter body is arbitrarily bended, to thereby increase the durability.

In addition, according to the present disclosure, a plurality of ring-shaped medical liquid distribution grooves extending in a circumferential direction of the catheter body are formed to be spaced apart from each other in the direction in which the catheter body extends, and the medical liquid discharge outlet is formed in each of the ring-shaped medical liquid distribution grooves, so that the medical liquid discharged through the medical liquid discharge outlet moves along the ring-shaped medical liquid distribution groove, that is, along the circumferential direction of the catheter body and is uniformly applied to the inner circumferential surface of the urethra, which makes the medicinal effect exert uniformly and quickly.

In addition, according to the present disclosure, a spiral medical liquid distribution groove spirally extending in a circumferential direction of the catheter body is formed in the direction in which the catheter body extends, and the medical liquid discharge outlet is formed in each of the spiral medical liquid distribution grooves, so that the medical liquid discharged through the medical liquid discharge outlet moves along the spiral medical liquid distribution groove, that is, along the circumferential direction of the catheter body and is uniformly applied to the inner circumferential surface of the urethra, which makes the medicinal effect exert uniformly and quickly.

In addition, according to the present disclosure, the medical liquid discharge outlets are formed to be spaced apart from each other on a virtual line that is on the circumferential surface parallel to a cross-sectional center line of the catheter body, and in a cross-sectional view of the catheter body, the medical liquid discharge outlets are formed to be inclined with respect to a radial direction of the catheter body, so that the medical liquid discharged through the medical liquid discharge outlets move more quickly along the medical liquid distribution grooves, to thereby quickly transfer the medicinal effect to the urethra.

In addition, according to the present disclosure, the medical liquid discharge outlets are formed to be alternately inclined in opposite directions about the radial direction of the catheter body along a longitudinal direction of the catheter body, so that although the medical liquid cannot move well in one circumferential direction due to the unusual situation inside the urethra, the medical liquid may move in an opposite direction, which allows the normal application of the medical liquid.

In addition, according to the present disclosure, the medical liquid discharge outlets are arranged on a virtual spiral along the circumferential surface of the catheter body, so that in a cross-sectional view of the catheter body, the locations of the medical liquid discharge outlets through which the medical liquid is discharged intensely are distributed in the circumferential direction of the catheter body and the medical liquid is applied much more uniformly in the circumferential direction of the catheter body.

MODE OF INVENTION

Hereinafter, preferred embodiments of the present disclosure will be described in detail with reference to the attached drawings.

Figure 3:
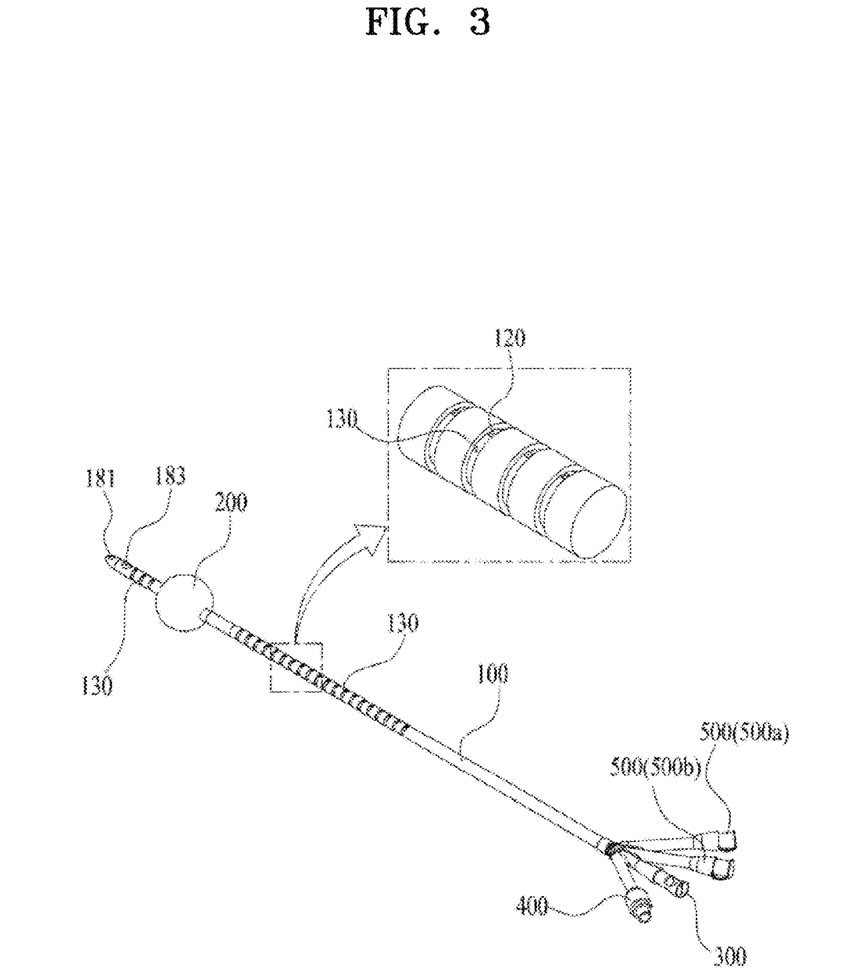
FIG. 3 is a perspective view illustrating a first embodiment of a medical liquid-injecting urinary catheter according to the present disclosure.
Figure 4:
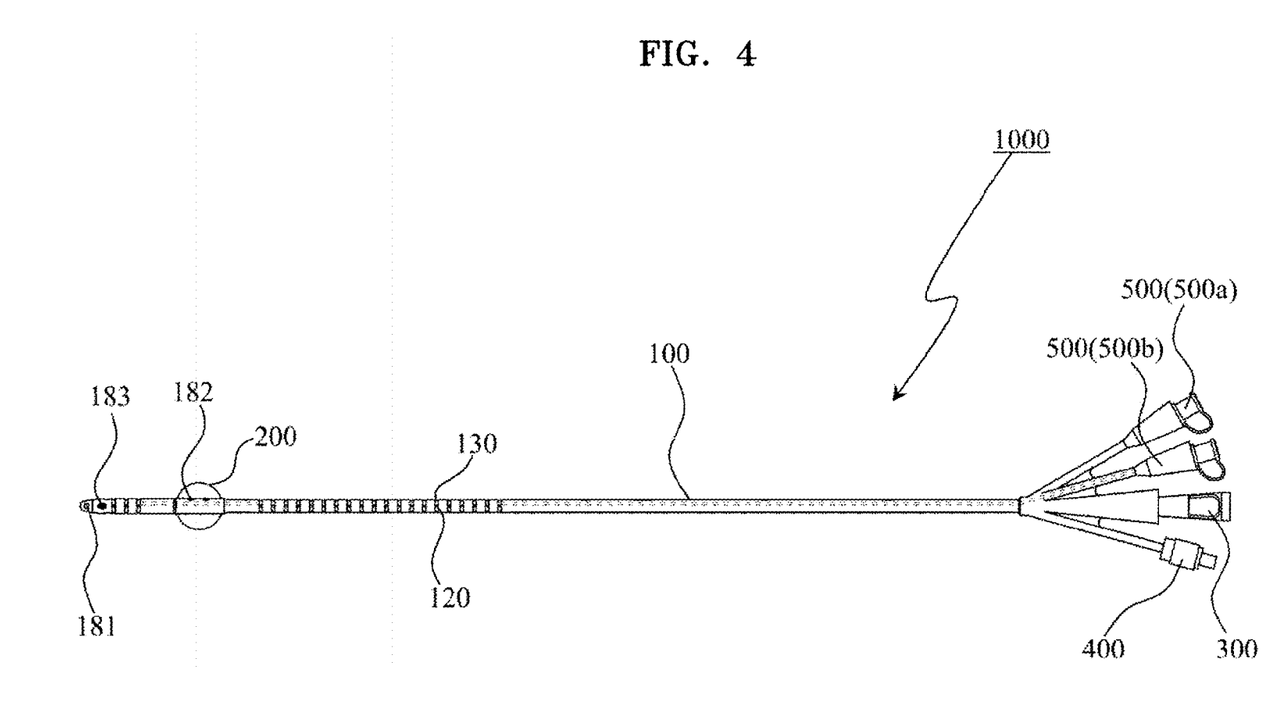
FIG. 4 is a plan view illustrating a first embodiment of a medical liquid-injecting urinary catheter according to the present disclosure.
Figure 5:
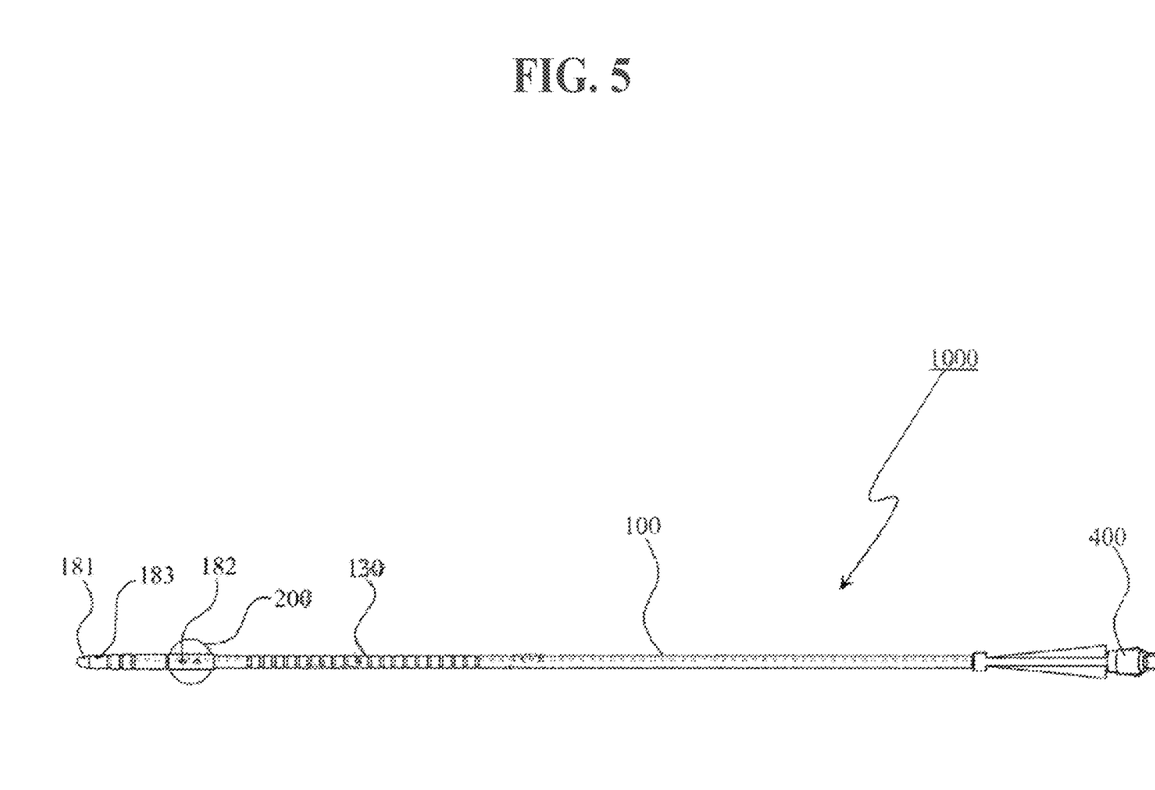
FIG. 5 is a front view illustrating a first embodiment of a medical liquid-injecting urinary catheter according to the present disclosure.

As illustrated in FIGS. 3 to 5, a medical liquid-injecting urinary catheter 1000 according to the present disclosure is provided for performing an involuntary urination function by making urine reach the bladder through the urethra of a patient, and includes a catheter body 100 that is flexible and has a hollow 110 pipe-shape, an inflation tube 200 positioned around one end of the catheter body 100 and spaced apart from the one end, a urination port 300 connected to the other end of the catheter body 100 to excrete urine out of the body, an air injection port 400 connected to the other end of the catheter body 100 and injecting air into the inflation tube 200, and a medical liquid-injection port 500 connected to the other end of the catheter body 100 and injecting the medical liquid.

Accordingly, the medical liquid-injecting urinary catheter 1000 is easily inserted into the urethra and has an effect of significantly reducing the occurrence of pain in the insertion.

The urination port 300 is a component for excreting urine from the bladder, the air injection port 400 inflates the inflation tube 200 by injecting air to prevent the urination catheter 1000 from easily falling out, and the medical liquid-injection port 500 is a component for injecting a medical liquid such as topical anesthetics, bladder irrigation fluid or bladder cleanser into the bladder and/or urethra.

Figure 6:
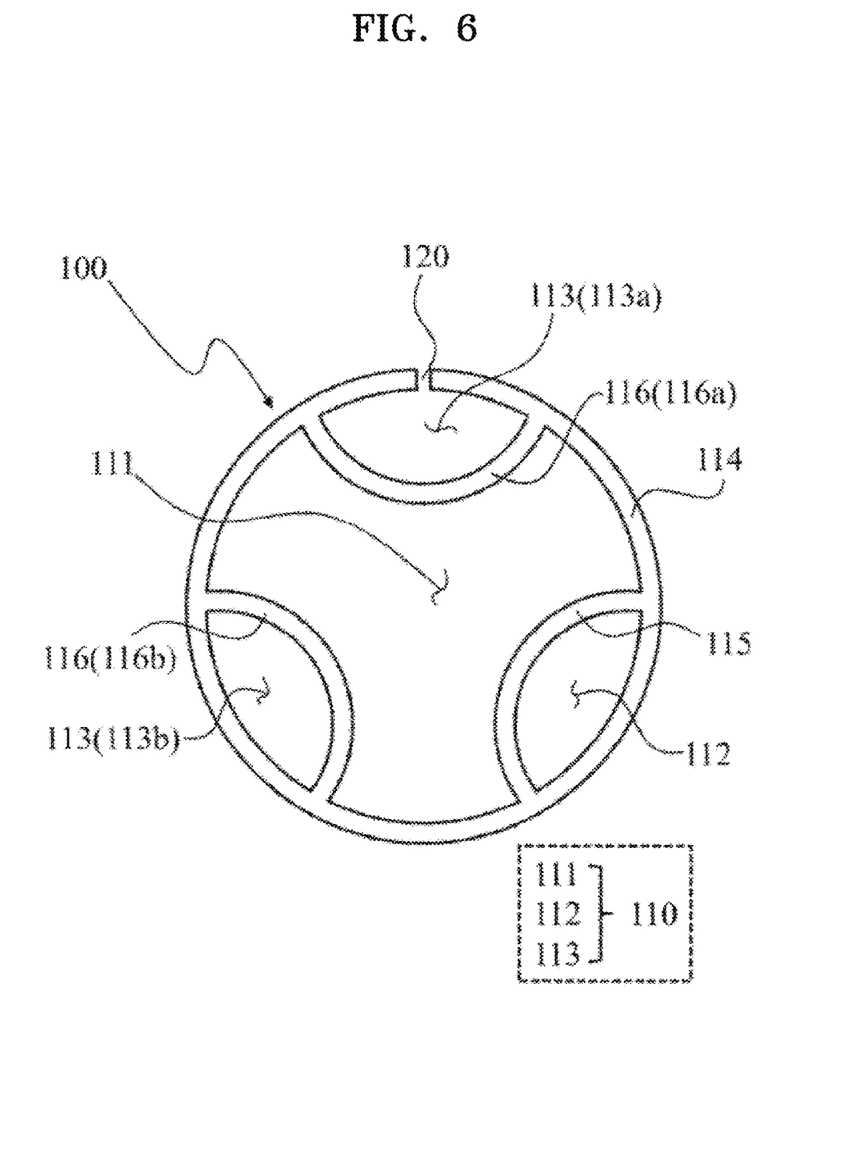
FIG. 6 is a cross-sectional view illustrating an embodiment of a catheter body in a first embodiment of a medical liquid-injecting urinary catheter according to the present disclosure.

As illustrated in FIG. 6, in a cross-sectional view of the hollow 110, the hollow 110 is composed of a urination hole 111 communicating with the urination port 300, an air injection hole 112 communicating with the air injection port 400, and a medical liquid-injection hole 113 communicating with the medical liquid-injection port 500, and the urination hole 111, the air injection hole 112, and the medical liquid-injection hole 113 are positioned in a separate state from each other.

To this end, in a cross-sectional view of the catheter body 100, the catheter body 100 includes a first tube 114 shaped as a circle and having inner and outer circumferential surfaces, a second tube 115 protruding from the inner circumferential surface of the first tube 114 in an arc shape to form the air injection hole 112, and a third tube 116 protruding from the inner circumferential surface of the first tube 114 in an arc shape to form the medical liquid-injection hole 113 and spaced apart from the second tube 115 in the circumferential direction, and the inside of the first tube 114, which is formed at outsides of the second tube 115 and the third tube 116, may form the urination hole 111.

According to the configuration, even if the catheter body 100 is arbitrarily bent, it is possible for the fluid to be separated and flow through the urination hole 111, the air injection hole 112, and the medical liquid-injection hole 113, and at the same time, the second tube 115 and the third tube 116 function as reinforcing ribs to maintain structural strength and durability.

That is, obstruction of the hollow 110 and topical pain caused by discontinuous bending of the catheter body 100 may be prevented, and durability may be increased.

On the circumferential surface of the catheter body 100, a plurality of medical liquid discharge outlets 120 are formed in such a way that the medical liquid discharge outlets 120 are communicated with the medical liquid-injection hole 113 and positioned to be spaced apart from each other in a direction in which the catheter body 100 extends and therefore, the medical liquid, which passes through the medical liquid-injection port 500 and the medical liquid-injection hole 113, is applied to the bladder or the urethra through the medical liquid discharge outlet 120, to thereby perform a predetermined function such as topical anesthesia, bladder irrigation fluid or bladder cleanser.

In the drawings, the medical liquid-injection hole 113 is configured to include a first medical liquid-injection hole 113a into which topical anesthetics flow and a second medical liquid-injection hole 113b into which a bladder irrigation fluid a bladder cleanser flows.

In addition, the third tube 116 is composed of a 3_1 tube 116a forming the first medical liquid-injection hole 113a and a 3_2 tube 116b forming the second medical liquid-injection hole 113b.

In relation to this, as illustrated in FIGS. 3 to 5, the medical liquid-injection port 500 includes a first medical liquid-injection port 500a through which topical anesthetics are supplied and a second medical liquid-injection port 500b through which a bladder irrigation fluid or a bladder cleanser is supplied.

However, the number of the medical liquid-injection holes 113 and the medical liquid-injection ports 500 may be one or three or more.

On the other hand, a plurality of ring-shaped medical liquid distribution grooves 130 extending in the circumferential direction of the catheter body 100 are formed to be spaced apart from each other in the direction in which the catheter body 100 extends, and the medical liquid discharge outlet 120 may be formed in each of the ring-shaped medical liquid distribution grooves 130.

In this case, only a single medical liquid discharge outlet 120 may be arranged in the ring-shaped medical liquid distribution groove 130 to increase the flow rate, so that the discharged medical liquid is preferably induced to rapidly diffuse.

Accordingly, the medical liquid discharged through the medical liquid discharge outlet 120 moves along the ring-shaped medical liquid distribution groove 130, that is, along the circumferential direction of the catheter body 100 and is uniformly applied to the inner circumferential surface of the urethra, which makes the medicinal effect exert uniformly and quickly.

Figure 11:
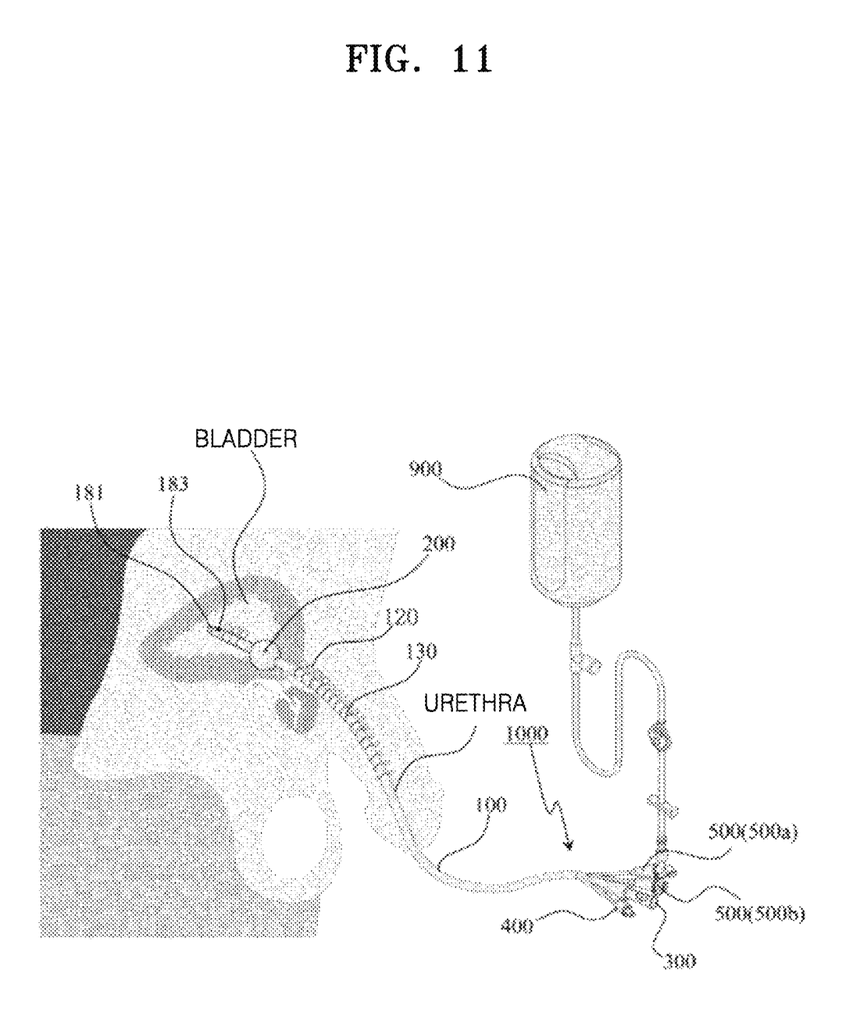
FIG. 11 is a use state view of a medical liquid-injecting urinary catheter according to the present disclosure.

As illustrated in FIG. 11, the medical liquid discharge outlet 120 is positioned on both sides of the inflation tube 200 to supply the medical liquid not only to the urethra but also to the bladder.

The medical liquid discharge outlet 120 is formed in the medical liquid distribution groove 130 but is illustrated as if the medical liquid discharge outlet 120 were separated from the medical liquid dispersion groove 130 in order to check the relative size of diameters.

Reference numeral 900 indicates a medical liquid supply tank for supplying the medical liquid to the medical liquid-injection port 500.

Figure 9:
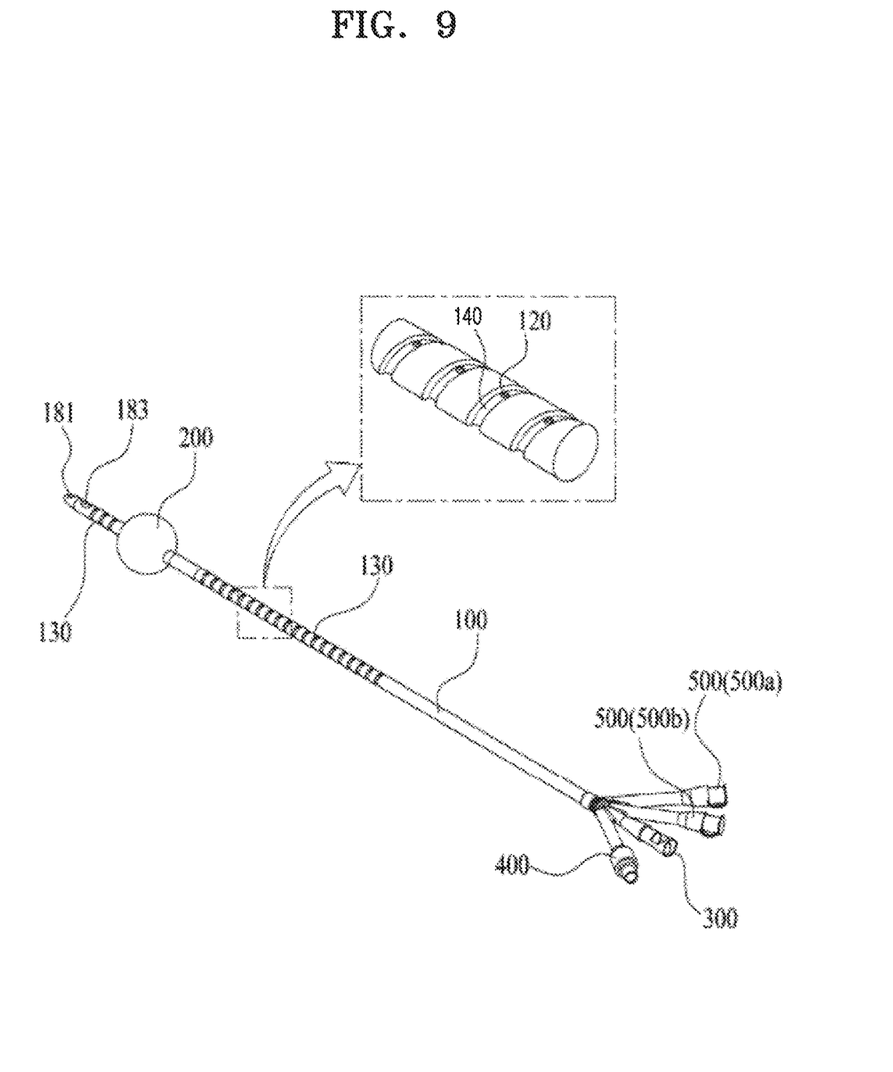
FIG. 9 is a perspective view illustrating a third embodiment of a medical liquid-injecting urinary catheter according to the present disclosure.
Figure 10:
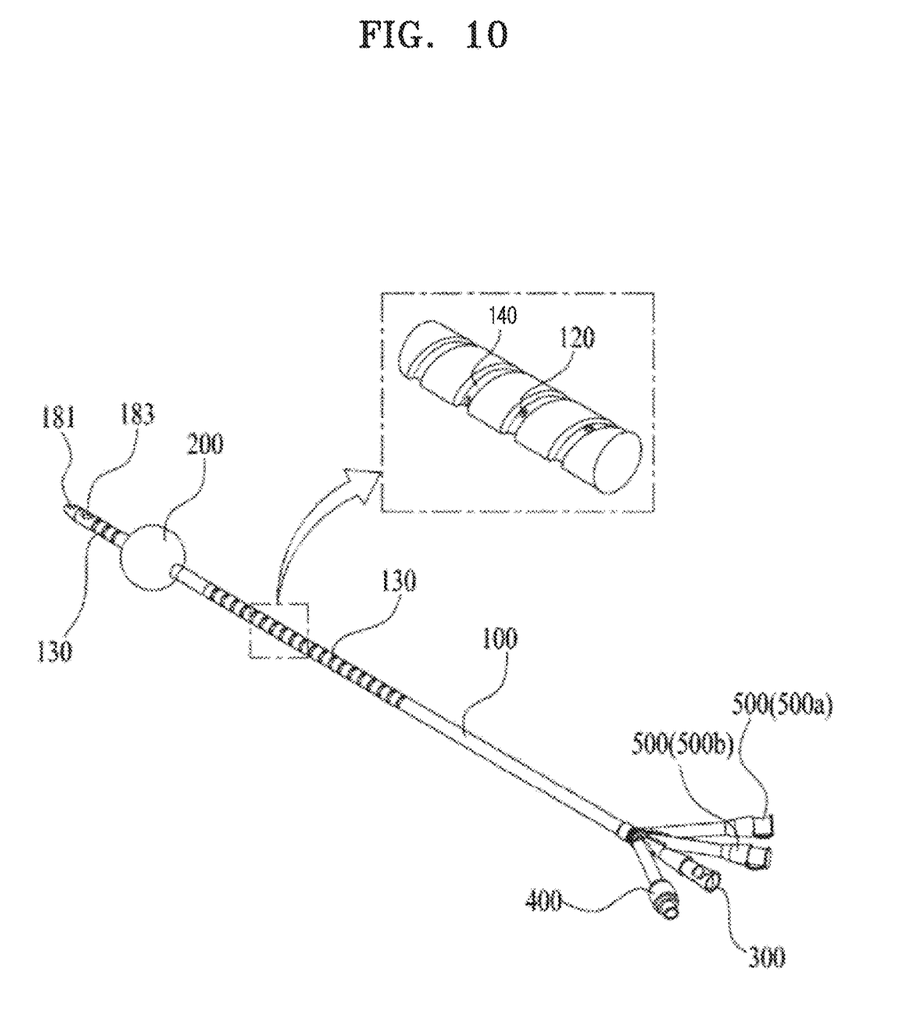
FIG. 10 is a perspective view illustrating a fourth embodiment of a medical liquid-injecting urinary catheter according to the present disclosure.

As another embodiment, as illustrated in FIGS. 9 and 10, a spiral medical liquid distribution groove 140 spirally extending along the circumferential direction of the catheter body 100 is formed along the direction in which the catheter body 100 extends, and the medical liquid discharge outlet 120 may be formed in each of the spiral medical liquid distribution grooves 140.

In this case, only a single medical liquid discharge outlet 120 is arranged along a single rotation of the spiral medical liquid distribution groove 140, so that the discharged medical liquid is preferably induced to rapidly diffuse.

Accordingly, the medical liquid discharged through the medical liquid discharge outlet 120 moves along the spiral medical liquid distribution groove 130, that is, along the circumferential direction of the catheter body 100 and is uniformly applied to the inner circumferential surface of the urethra, which makes the medicinal effect exert uniformly and quickly.

In addition, as illustrated in FIGS. 3 and 9, the medical liquid discharge outlets 120 are formed to be spaced apart from each other on a virtual line that is on the circumferential surface parallel to the cross-sectional center line of the catheter body 100, and in a cross-sectional view of the catheter body 100, the medical liquid discharge outlets 120 may be formed to be inclined with respect to a radial direction of the catheter body 100.

According to the configuration described above, the medical liquid discharged through the medical liquid discharge outlets 120 move more quickly along the medical liquid distribution grooves 130 and 140, to thereby transfer the medicinal effect to the urethra quickly.

Figure 7:
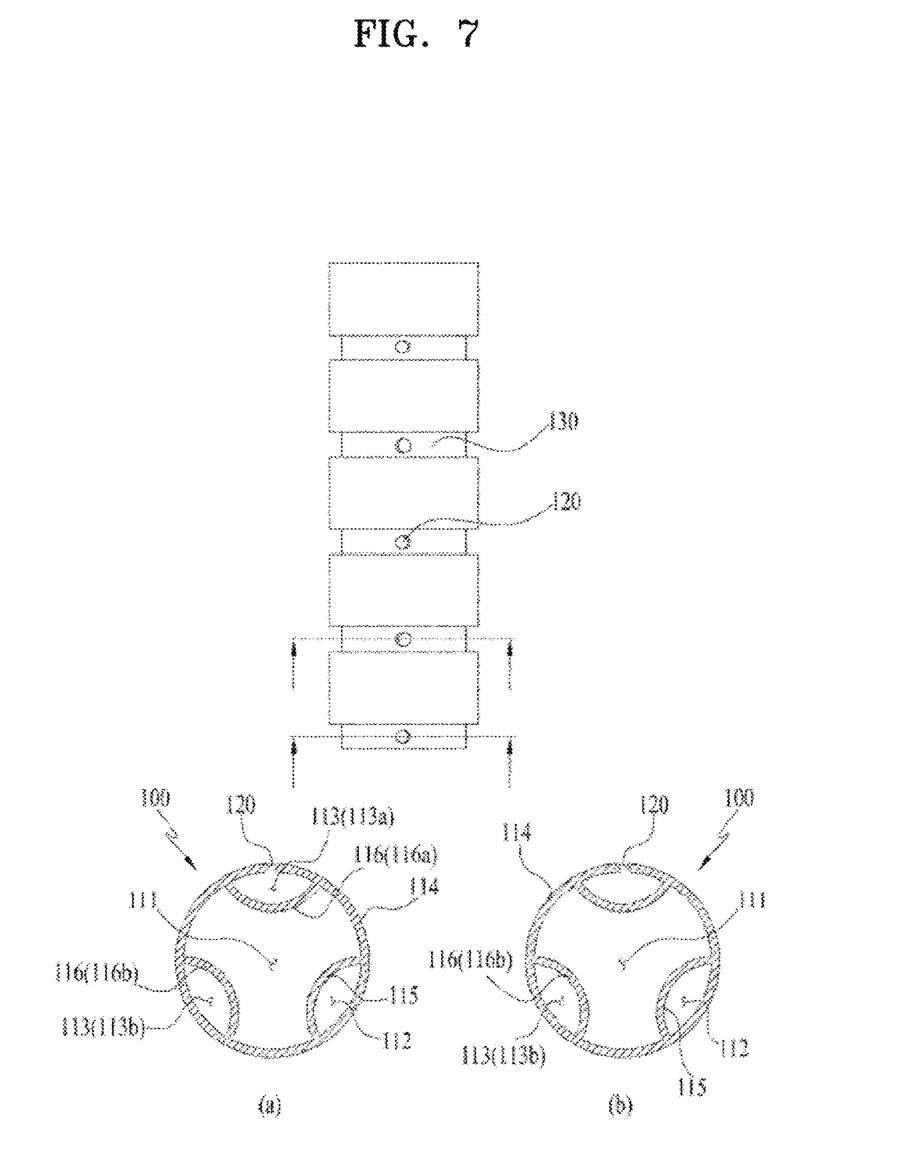
FIG. 7 is a cross-sectional view illustrating another embodiment of a catheter body in a first embodiment of a medical liquid-injecting urinary catheter according to the present disclosure.

Moreover, as illustrated in FIG. 7, the plurality of medical liquid discharge outlets 120 are formed to be alternately inclined in opposite directions about the radial direction of the catheter body 100 along the longitudinal direction of the catheter body 100, so that although the medical liquid cannot move well in one circumferential direction due to the unusual situation inside the urethra, the medical liquid may move in an opposite direction, which allows the normal application of the medical liquid.

Figure 8:
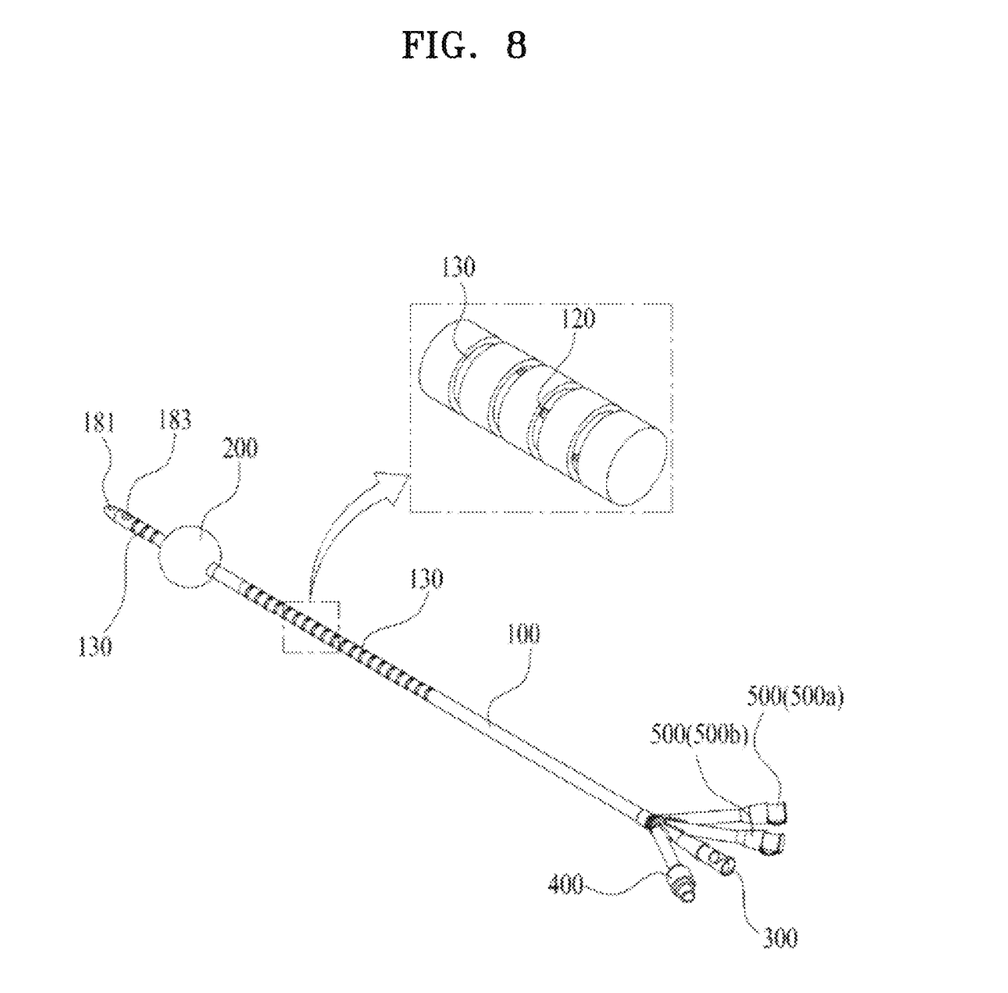
FIG. 8 is a perspective view illustrating a second embodiment of a medical liquid-injecting urinary catheter according to the present disclosure.

On the other hand, as illustrated in FIGS. 8 and 10, a plurality of medical liquid discharge outlets 120 may be arranged on a virtual spiral along the circumferential surface of the catheter body 100.

Accordingly, in a cross-sectional view of the catheter body 100, the locations of the medical liquid discharge outlets 120 through which the medical liquid is discharged intensely are distributed in the circumferential direction of the catheter body 100, so that the medical liquid may be applied much more uniformly in the circumferential direction of the catheter body 100.

In this case, as illustrated in FIG. 10, when the spiral medical liquid distribution grooves 140 are formed to be spirally extending in the circumferential direction of the catheter body 100, the medical liquid discharge outlets 120 may be positioned on the spiral.

On the other hand, as illustrated in FIG. 11, the cross-sectional area or diameter of the medical liquid discharge outlet 120 is configured to gradually increase from the other end of the catheter body 100 toward the inflation tube 200, so that the injection amount decrease caused by pressure loss is preferably prevented when the medical liquid flows.

For example, the diameter of the medical liquid discharge outlet 120 may be set to continuously increase from 0.01 mm to 0.1 mm, and two or more medical liquid discharge outlets 120 are allowed to have the same diameter.

The diameter of the medical liquid discharge outlet 120 facing the bladder may remain the same as the diameter of the medical liquid discharge outlet 120 that is closest to the inflation tube 200 on the urethra side.

In FIG. 5, a reference numeral 181, which is not described, is a first penetrating hole formed in the catheter body 100 and communicating with the urination hole 111, a reference numeral 182 is a second penetrating hole formed in the catheter body 100 and communicating with the air injection hole 112, and a reference numeral 183 is a third penetrating hole formed in the catheter body 100 and communicating with the second medical liquid-injection hole 113b.

Urine in the bladder is excreted to the outside through the first penetrating hole 181, air is supplied to the inflation tube 200 through the second penetrating hole 182, and the medical liquid such as bladder irrigation fluid or bladder cleanser, etc. is supplied through the third penetrating hole 183.

The present disclosure described above is not limited to the embodiments described above and the accompanying drawings, and it will be clear to a person with ordinary skill in the art that various substitutions, modifications, and changes are possible without departing from the technical spirit of the present disclosure.

The invention claimed is:

1. A medical liquid-injecting urinary catheter comprising:
 a catheter body that is flexible and has a hollow tubular shape;
 a retention balloon positioned around one end of the catheter body and spaced apart from the one end;
 a urination port connected to the other end of the catheter body and configured to transport urine out of the body;
 an air injection port connected to the other end of the catheter body and configured to inject air into the retention balloon; and
 a medical liquid-injection port connected to the other end of the catheter body and configured to inject a medical liquid,
 wherein,
 in a cross-sectional view of the catheter body, a urination lumen communicating with the urination port, an air injection lumen communicating with the air injection port, and a medical liquid-injection lumen communicating with the medical liquid-injection port are arranged to be separated from each other, and a plurality of medical liquid discharge outlets are formed on a circumferential surface of the catheter body in such a configuration that the plurality of medical liquid discharge outlets communicate with the medical liquid-injection lumen and are spaced apart from each other in a direction in which the catheter body extends, and a spiral medical liquid distribution groove spirally extending in a circumferential direction of the catheter body is formed in the direction in which the catheter body extends, and the medical liquid discharge outlets are arranged on intersection points where a virtual line parallel to the direction in which the catheter body extends intersects the spiral medical liquid distribution groove, rather than on the circumferential surface where the spiral medical liquid distribution groove is not formed, and the spiral medical liquid distribution groove comprises a first spiral groove, which extends around the catheter body for at least one rotation on one side of the retention balloon, and a second spiral groove, which extends around the catheter body for at least one rotation on a side opposite to the one side of the retention balloon, and the medical liquid discharge outlets comprise at least one first outlet formed on the first spiral groove, and at least one second outlet formed on the second spiral groove.

2. The medical liquid-injecting urinary catheter of claim 1, wherein the discharge outlets are tilted at a non-perpendicular angle relative to a radial direction of the catheter body.

3. The medical liquid-injecting urinary catheter of claim 2, wherein the medical liquid discharge outlets are formed to be alternately inclined in opposite directions about the radial direction of the catheter body along a longitudinal direction of the catheter body.

4. The medical liquid-injecting urinary catheter of claim 1, wherein, in a cross-sectional view of the catheter body, the catheter body includes a first tube shaped as a circle and having inner and outer circumferential surfaces, a second tube protruding from the inner circumferential surface of the first tube in an arc shape to form the air injection lumen, and a third tube protruding from the inner circumferential surface of the first tube in an arc shape to form the medical liquid-injection lumen and spaced apart from the second tube in the circumferential direction, wherein inner walls of the first tube and outer walls of the second tube and the third tube form the urination lumen.

5. The medical liquid-injecting urinary catheter of claim 4, wherein the first tube, second tube, and the third tube are positioned in a separate state from each other.

6. The medical liquid-injecting urinary catheter of claim 1, wherein the medical liquid discharge outlets are not extended to the urinary port.

7. The medical liquid-injecting urinary catheter of claim 1, wherein the medical liquid discharge outlets are positioned on both sides of the retention balloon.

8. The medical liquid-injecting urinary catheter of claim 1, wherein each of the medical liquid discharge outlets is arranged along a single rotation of the spiral medical liquid distribution groove.

9. The medical liquid-injecting urinary catheter of claim 1, wherein a diameter of the medical liquid discharge outlet is configured to gradually increase from the other end of the catheter body toward the retention balloon.

10. The medical liquid-injecting urinary catheter of claim 9, wherein a size of the diameter of the medical liquid discharge outlet is from 0.01 mm to 0.1 mm.

11. The medical liquid-injecting urinary catheter of claim 9, wherein the diameter of the medical liquid discharge outlet is configured to gradually increase from 0.01 mm to 0.1 mm.

12. The medical liquid-injecting urinary catheter of claim 1, wherein the medical liquid-injection port is one or more.

13. The medical liquid-injecting urinary catheter of claim 1, wherein the medical liquid discharge outlets are uniformly spaced apart from each other.

14. A method injecting liquid through a medical liquid-injecting urinary catheter of claim 1, wherein a flow rate of the liquid is increased compared to using a urinary catheter without a spiral medical liquid distribution groove spirally extending in a circumferential direction of the catheter body that is formed in the direction in which the catheter body extends, and the medical liquid discharge outlets are arranged on intersection points where a virtual line parallel to the direction in which the catheter body extends intersects the spiral medical liquid distribution groove.

15. The method of claim 14, wherein the method uniformly applies the liquid to an inner circumferential surface of a urethra.

16. The method of claim 15, wherein the method quickly produces a uniform medicinal effect.

17. A medical liquid-injecting urinary catheter comprising:

a catheter body that is flexible and has a hollow tubular shape;

a retention balloon positioned around one end of the catheter body and spaced apart from the one end;

wherein, in a cross-sectional view of the catheter body, a urination lumen communicating with an urination port, an air injection lumen communicating with an air injection port, and a medical liquid-injection lumen communicating with a medical liquid-injection port are arranged to be separated from each other, and a plurality of medical liquid discharge outlets are formed on a circumferential surface of the catheter body in such a configuration that the plurality of medical liquid discharge outlets communicate with the medical liquid-injection lumen and are spaced apart from each other in a direction in which the catheter body extends, and a spiral medical liquid distribution groove spirally extending in a circumferential direction of the catheter body is formed in the direction in which the catheter body extends, and the medical liquid discharge outlets are arranged only on intersection points where a virtual line parallel to the direction in which the catheter body extends intersects the spiral medical liquid distribution groove, and the spiral medical liquid distribution groove comprises a first spiral groove, which extends around the catheter body for at least one rotation on one side of the retention balloon, and a second spiral groove, which extends around the catheter body for at least one rotation on a side opposite to the one side of the retention balloon, and the medical liquid discharge outlets comprise at least one first outlet formed on the first spiral groove, and at least one second outlet formed on the second spiral groove.

18. A medical liquid-injecting urinary catheter comprising:
a catheter body that is flexible and has a hollow tubular shape;
a urination port connected to one end of the catheter body and configured to transport urine out of the body;
an air injection port connected to the one end of the catheter body and configured to inject air into a retention balloon; and
a medical liquid-injection port connected to the one end of the catheter body and configured to inject a medical liquid,
wherein,
in a cross-sectional view of the catheter body, a urination lumen communicating with the urination port, an air injection lumen communicating with the air injection port, and a medical liquid-injection lumen communicating with the medical liquid-injection port are arranged to be separated from each other, and
a plurality of medical liquid discharge outlets are formed on a circumferential surface of the catheter body in such a configuration that the plurality of medical liquid discharge outlets communicate with the medical liquid-injection lumen and are spaced apart from each other in a direction in which the catheter body extends, and
a spiral medical liquid distribution groove spirally extending in a circumferential direction of the catheter body is formed in the direction in which the catheter body extends, and
the medical liquid discharge outlets are arranged on intersection points where a virtual line parallel to the direction in which the catheter body extends intersects the spiral medical liquid distribution groove, rather than on the circumferential surface where the spiral medical liquid distribution groove is not formed, and
the spiral medical liquid distribution groove comprises a first spiral groove, which extends around the catheter body for at least one rotation on one side of the retention balloon, and a second spiral groove, which extends around the catheter body for at least one rotation on a side opposite to the one side of the retention balloon, and
the medical liquid discharge outlets comprise at least one first outlet formed on the first spiral groove, and at least one second outlet formed on the second spiral groove.

19. The medical liquid-injecting urinary catheter of claim 18, wherein the retention balloon is positioned to the other end of the catheter body.

* * * * *